United States Patent
Bhatia

(10) Patent No.: US 6,867,296 B2
(45) Date of Patent: Mar. 15, 2005

(54) RECOVERY AND PURIFICATION OF ANHYDRO SUGAR ALCOHOLS FROM A VAPOR STREAM

(75) Inventor: Kamlesh Kumar Bhatia, Newark, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 10/414,606

(22) Filed: Apr. 16, 2003

(65) Prior Publication Data

US 2004/0030161 A1 Feb. 12, 2004

Related U.S. Application Data

(60) Provisional application No. 60/373,102, filed on Apr. 17, 2002.

(51) Int. Cl.[7] .......................... C07G 17/00; C07H 1/00; C07H 3/00; C08B 37/00; C13K 5/00
(52) U.S. Cl. .................... 536/126; 536/124; 536/123.1; 536/55.3; 536/18.5; 536/18.6; 536/18.7; 549/464; 424/401; 424/451; 428/36.92; 514/338
(58) Field of Search ................................. 536/126, 124, 536/123.1, 55.3, 18.5, 18.6, 18.7; 549/464; 424/401, 451; 514/338; 428/36, 92

(56) References Cited

U.S. PATENT DOCUMENTS

| 4,564,692 | A | | 1/1986 | Feldmann et al. |
| 6,407,266 | B2 | * | 6/2002 | Bhatia .......................... 549/464 |
| 6,639,067 | B1 | * | 10/2003 | Brinegar et al. ............ 536/126 |

FOREIGN PATENT DOCUMENTS

| WO | WO 00/14081 | 3/2000 |
| WO | WO 00/41985 | 7/2000 |

OTHER PUBLICATIONS

Beck, et al., "Acid Catalyzed Dehydration of Alditols, Part I. D–Glucitol and D–Mannitol", Acta Chemica Scandinavica B, 1981, pp. 441–449, vol. 35, Lyngby, Denmark.

International Search Report dated Apr. 17, 2003.

* cited by examiner

Primary Examiner—James O. Wilson
Assistant Examiner—Devesh Khare

(57) ABSTRACT

This invention concerns a process for recovering and purifying dianhydro sugar alcohols from a vapor stream comprising dianhydro sugar alcohols, such as isosorbide, and water vapor.

19 Claims, 2 Drawing Sheets

RECOVERY AND PURIFICATION OF ANHYDRO SUGAR ALCOHOLS FROM A VAPOR STREAM

FIELD OF THE INVENTION

This invention concerns a process for recovering and purifying dianhydro sugar alcohols from a vapor stream comprising dianhydro sugar alcohols, such as isosorbide, and water vapor.

TECHNICAL BACKGROUND OF THE INVENTION

Anhydro sugar alcohols, in particular derivatives of mannitol, iditol, and sorbitol, are known for their therapeutic uses and uses in food. At least one of these, isosorbide, 1,4:3,6-dianhydrosorbitol, is useful as a monomer in the manufacture of polymers and copolymers, especially polyester polymers and copolymers.

Anhydro sugar alcohols are produced by dehydration of the corresponding sugar alcohols (or monoanhydro sugar alcohols) by the action of various dehydration catalysts, typically strong acid catalysts.

Batch processes for the preparation of dianhydro sugar alcohols by acid dehydration are known in the art. For example, a batch process for the formation of the dianhydro sugar alcohol isosorbide has been described as a two-step process involving intramolecular dehydration of sorbitol to sorbitan (1,4-monoanhydrosorbitol), and further reaction of sorbitan to isosorbide (1,4:3,6-dianhydrosorbitol) in an acid-catalyzed dehydration-cyclization (R. Beck, *Pharm. Mfg Inc.* (1996), 97–100). Other monoanhydro by-products, 2,5-anhydro-L-iditol and 2,5-anhydro-D-mannitol, are also known to be produced under some reaction conditions (K. Bock et al., *Acta. Chem. Scand.* B 35, 441–449 (1981)).

For isosorbide to be used as a monomer in high volume polymers and copolymers for applications such as containers, it needs to be produced in large quantities, preferably in a continuous process.

International Patent Application WO 00/14081 describes a continuous process for producing anhydro sugar alcohols in which an organic solvent is used to dissolve the product and remove it from the reaction vessel.

U.S. Pat. No. 6,407,266 describes a continuous process for the dehydration of sugar alcohols. Purification of the crude reaction product may be accomplished by distillation, recrystallization, melt crystallization or a combination thereof.

The crude reaction product of prior art processes, as practiced using sorbitol, comprises about 70 to 80% by weight isosorbide and 20 to 30% byproducts. Several separation and purification processes for isosorbide have been disclosed in the prior art, including, for example, distillation, crystallization, chromatographic separation, and ion exchange. U.S. Pat. No. 4,564,692 discloses a process using crystallization from aqueous solutions to obtain the high purity needed for applications as polyol components in polyester and polyurethane polymers.

Commonly assigned U.S. Provisional Application No. 60/373,106 filed of even date herewith, discloses a combined reaction-separation process wherein dianhydro sugar alcohols are obtained as vapors in a stream of water vapor. The isosorbide condensed from such a vapor streams would require further purification to obtain the high level of purity needed for use in polymers such as polyesters, that is, at least 99.8% pure.

It is the object of the present invention to provide a novel, effective means of recovering and purifying dianhydro sugar alcohols from aqueous vapor streams, wherein purification by crystallization occurs while recovering the product by condensation, and a separate crystallization step is eliminated.

SUMMARY OF THE INVENTION

In accordance with the object of this invention, there is provided a process for the recovery and purification of a dianhydro sugar alcohol from a vapor stream of the dianhydro sugar alcohol and water, comprising partially condensing the vapor stream under controlled temperature and reduced pressure, such that most of the dianhydro sugar alcohol is condensed as a supersaturated solution and forms high purity crystals, after which the crystals are separated and the mother liquor is recycled.

In one embodiment of this invention, the process comprises:

a) introducing a vapor stream comprising a dianhydro sugar alcohol and water into a condensation/crystallization vessel maintained at a reduced pressure and at a temperature below the melting point of the dianhydro sugar alcohol;

b) partially condensing the vapor stream to precipitate most of the dianhydro sugar alcohol as a slurry of high purity dianhydro sugar alcohol crystals in a supersaturated mother liquor;

c) removing uncondensed vapors from the condensation vessel;

d) withdrawing the slurry of high purity dianhydrosugar alcohol crystals from the condensation-crystallization vessel; and e) separating the dianhydro sugar alcohol crystals from the slurry.

DETAILED DESCRIPTION OF THE INVENTION

The present disclosure describes a novel, effective, and economical process for recovering high purity dianhydro sugar alcohols, most preferably isosorbide, from a vapor stream.

The process is generally directed toward the production of high purity dianhydro sugar alcohols as may be required for use in polymerization processes, such as polyester production. The feed stream for the process of the present invention is generally a vapor stream of 98–99% purity dianhydro sugar alcohols along with water vapor evolved through reaction and evaporation, as described in commonly assigned U.S. Provisional Application No. 60/373,106. Such streams may contain 20–30% by weight dianhydro sugar alcohol product, the balance being water vapor. Product recovery and further purification according to the prior art would generally require condensing the vapor stream to recover the product as a 20–30% solution, concentrating this solution, and subjecting it to one or more purification steps. It is known to purify anhydro sugar alcohols by crystallization, for example, from methanol or from aqueous solution, as disclosed in U.S. Pat. No. 4,564,692. However, this requires concentrating the solution to greater than 90% by weight dianhydro sugar alcohol, seeding the concentrated solution, and then cooling it.

It has now been discovered that dianhydro sugar alcohols can be recovered from a vapor stream and concurrently purified by partially condensing the vapor stream under controlled temperature and reduced pressure. Under these conditions, almost all of the dianhydro sugar alcohol is condensed, but most of the water remains in the vapor state. Furthermore, the condensate is a supersaturated solution that forms dianhydro sugar alcohol crystals of higher purity than in prior art processes, leaving behind in solution the more polar impurities, such as the monoanhydro sugar alcohols (sorbitan in the case of isosorbide) and the color-forming species volatilized from the reaction mass. The present invention thus provides an improved process wherein condensation and subsequent vaporization of all the water is unnecessary, and the need for separate crystallization step is eliminated.

Figure 1:
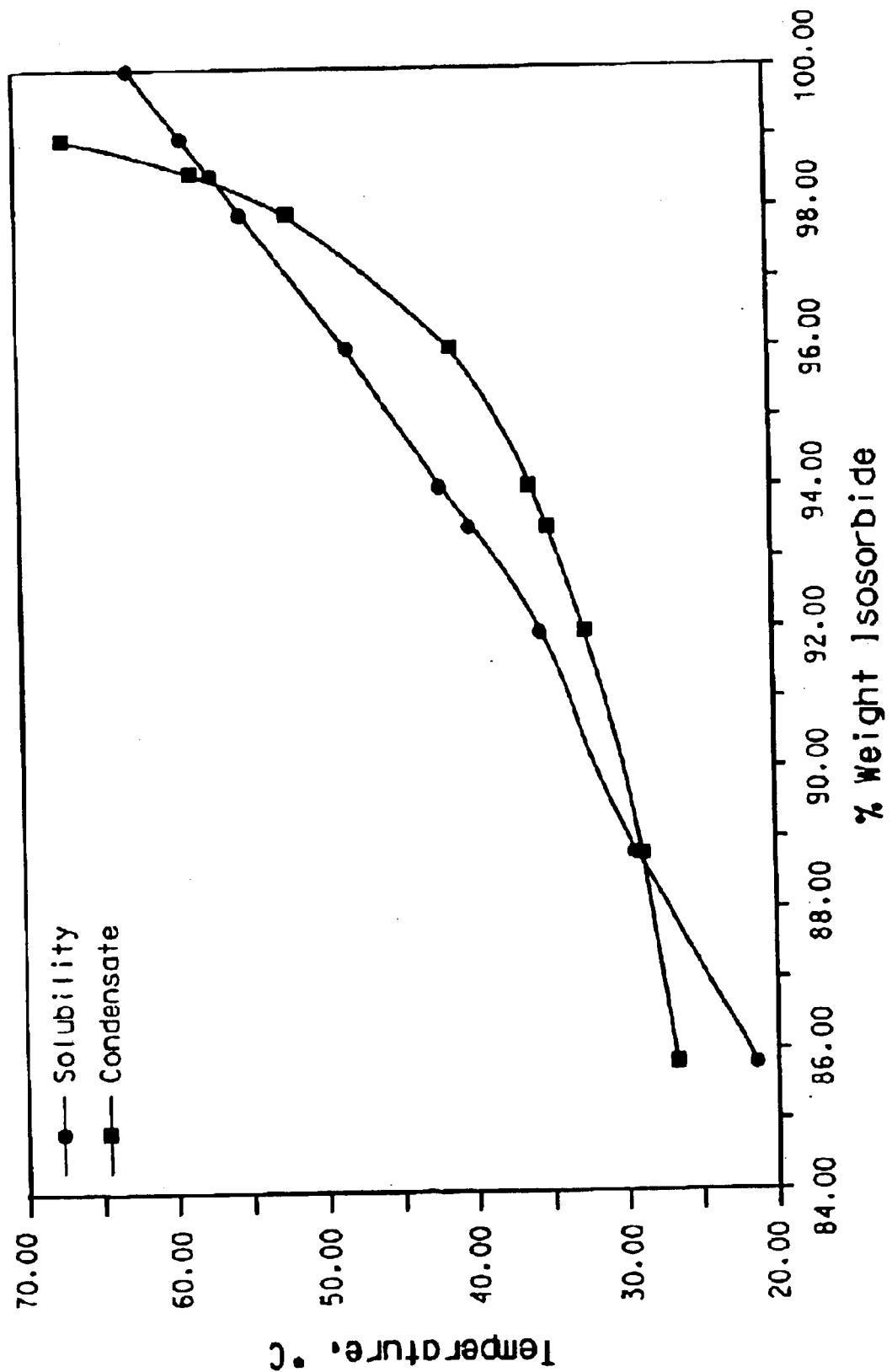
FIG. 1 shows the solubility of isosorbide in water and its concentration in the condensate in the process of the present invention.

The basis for this process is illustrated for isosorbide in FIG. 1, where the upper curve represents the solubility of isosorbide in water (as percent by weight isosorbide) on the x-axis vs. temperature on the y-axis. The lower curve represents the composition of the condensate (as percent by weight isosorbide) when the condensation is conducted at a pressure of about 14 mm Hg. These curves show that isosorbide is highly soluble in water and that its solubility approaches 100% (i.e., completely soluble) as the temperature approaches the melting point of isosorbide, about 62° C. The condensate is a highly concentrated solution of isosorbide and contains only a small fraction as water. Thus, by conducting the condensation under these conditions, most of the isosorbide from, for example, a 20–30 weight percent isosorbide aqueous vapor stream is recovered, leaving most of the water in the vapor phase. The amount of isosorbide left in the vapor is negligibly small because of the very low vapor pressure of isosorbide, on the order of only about 0.001 mm Hg, at a condensation temperature of about 45° C.

Furthermore, FIG. 1 shows that at a temperature between about 30° C. and 56° C., the condensate is supersaturated, i.e., the concentration of isosorbide is greater than its solubility. The isosorbide can then precipitate as crystals. Appropriate choice of the condensation temperature allows control of the degree of supersaturation so as to obtain an optimum balance of nucleation and crystal growth rates, crystal-to-mother liquor ratio, and product purity desired for a particular application. The appropriate balance can be determined experimentally within the temperature range that gives supersaturated condensate. Generally, a temperature at the high end of the range is preferred for ease of cooling, lower solution viscosity, and speed of crystallization. A higher degree of supersaturation gives faster nucleation and crystal growth rates, but the purity of the crystals may suffer if crystal growth is too fast. Under the 14 mm pressure conditions of FIG. 1, the preferred temperature range is about 33° C. to about 48° C., most preferably from 37° C. to 45° C. Temperatures best suited for other dianhydro sugar alcohols can easily be determined by similar experimental procedures.

The optimum condensation temperature range can be varied by changing the condensation pressure. Lower pressures give a wider temperature range and higher degree of supersaturation but may require refrigeration to condense the water vapor leaving the condensation/crystallization vessel. For example, at about 9 mm Hg, the temperature range may be from 20 to 55° C., preferably between 25 and 50° C. Higher pressures are advantageous for subsequent water condensation but result in a narrower temperature range for product recovery and crystallization. Under higher pressures, more water is condensed during the partial condensation and the solution is less supersaturated. Generally, the partial condensation pressure for recovery and crystallization is from about 5 to 30 mm Hg, preferably from 10 to 20 mm Hg, and most preferably from 12 to 18 mm Hg. Similar processes can be used for determining the appropriate conditions for other anhydro sugar alcohols.

The process of the present invention can be conducted batchwise or continuously. It is preferably conducted continuously, in a process comprising:

a) continuously feeding the vapor stream of water and dianhydro sugar alcohol to a condensation vessel maintained at the preferred temperature and pressure;

b) continuously condensing a portion of the stream to condense most of the dianhydro sugar alcohol as a supersaturated solution;

c) allowing a portion of the dianhydro sugar alcohol to precipitate as dianhydro sugar alcohol crystals, to produce a slurry of dianhydro sugar alcohol crystals in a supersaturated solution;

d) continuously withdrawing the slurry of dianhydro sugar alcohol crystals from the vessel;

e) continuously withdrawing the uncondensed vapors from the condensation vessel to maintain the desired pressure;

f) continuously condensing the uncondensed vapors in a secondary condenser connected to a vacuum source to withdraw any noncondensibles;

g) continuously separating the dianhydro sugar alcohol crystals from the slurry; and h) recycling the mother liquor back to the condensation vessel.

The crystals may be separated from the solution by means known in the art, such as filtration and centrifugation. For best purity, the product cake is preferably washed to displace the mother liquor. Since anhydro sugar alcohols are highly soluble in water, it is preferred that very cold, demineralized water, or, more preferably, a solution of purified dianhydro sugar alcohols be used for the washing.

A portion of the mother liquor may be purged before recycling back to the condensation vessel to remove impurities, such as color-forming moieties, from the system and to maintain the impurities at a low level in the slurry. The amount of purge depends upon the purity of crystals desired for a particular application. Higher purge results in a lower level of impurities in the slurry and higher purity crystals. The purged mother liquor may be treated to remove the impurities and recycled to the condensation vessel or used in applications for which purity is not very critical. All or a portion of the mother liquor may also be subjected to fractional crystallization to recover more crystals before it is recycled, if the somewhat lower purity crystals thus obtained are suitable for a desired use.

In another embodiment of the process of the present invention, the condensate obtained by partial condensation of the vapor stream is withdrawn from the condensation vessel as a concentrated solution and allowed to crystallize in a separate crystallizer or subjected to fractional crystallization. This may be useful for obtaining a higher concentration of solids in the slurry and reducing the liquid load on the solid liquid device. Allowing the crystallization to occur in the condensation vessel itself is preferred for economic reasons as it eliminates the need for a separate crystallizer.

Partial condensation for the process of the present invention may be conducted in a condensation device of any design known in the art. A preferred device is a direct contact condenser, wherein the vapors to be condensed are intimately contacted with a cooling liquid. Such direct contact may be achieved by bubbling the vapor through the liquid or by spraying the liquid into the vapor, or by flowing the liquid as films in the vapor, or by employing a combination of such means.

The heat evolved in condensation and crystallization may be removed by any heat exchange means known in the art. A preferred method, particularly for large-scale operation, is to circulate the liquid through a heat exchanger external to the condensation vessel. The liquid in the case of partial condensation of dianhydro sugar alcohols would be the condensate itself, preferably the mother liquor.

In a preferred embodiment of the process of the present invention, heat removal required for condensation and crystallization is achieved by simply injecting fresh water into the vessel to contact the vapors. Under the reduced pressure and the operating temperature of the vessel, this excess water gets evaporated using the heat of the process fluid. This preferred means of cooling eliminates the need for an external recirculation exchanger. It also improves process reliability by eliminating cooling the mother liquor from which dianhydro sugar alcohols may crystallize and deposit on exchanger tubes at low velocities. It is preferred that the water used for cooling has been purified, preferably demineralized, so external impurities are not introduced into the system when a highly pure product is desired. The water may be introduced directly into the condensation vessel, for example, as a spray, or injected into the recycled mother liquor stream or a circulating condensate/slurry stream, or a combination of the above.

In a preferred condenser-crystallizer design particularly suited for large-scale production, all or a part of the vapor stream is sparged into the condensate, i.e., the slurry phase, most preferably under one or more draft tubes. The vapor bubbles rising though the draft tubes provide intimate contact, circulate the slurry up and around, and keep the crystals in suspension for uniform growth. The vessel thereby behaves like a draft tube crystallizer without the need for an internal circulation/suspension impeller, and high concentrations of crystals can be maintained to reduce the liquid load on the solid-liquid (i.e., crystals-mother liquor) separation device. The solids concentration in the slurry is generally 10–30% by weight, preferably 15–25% by weight.

Figure 2:
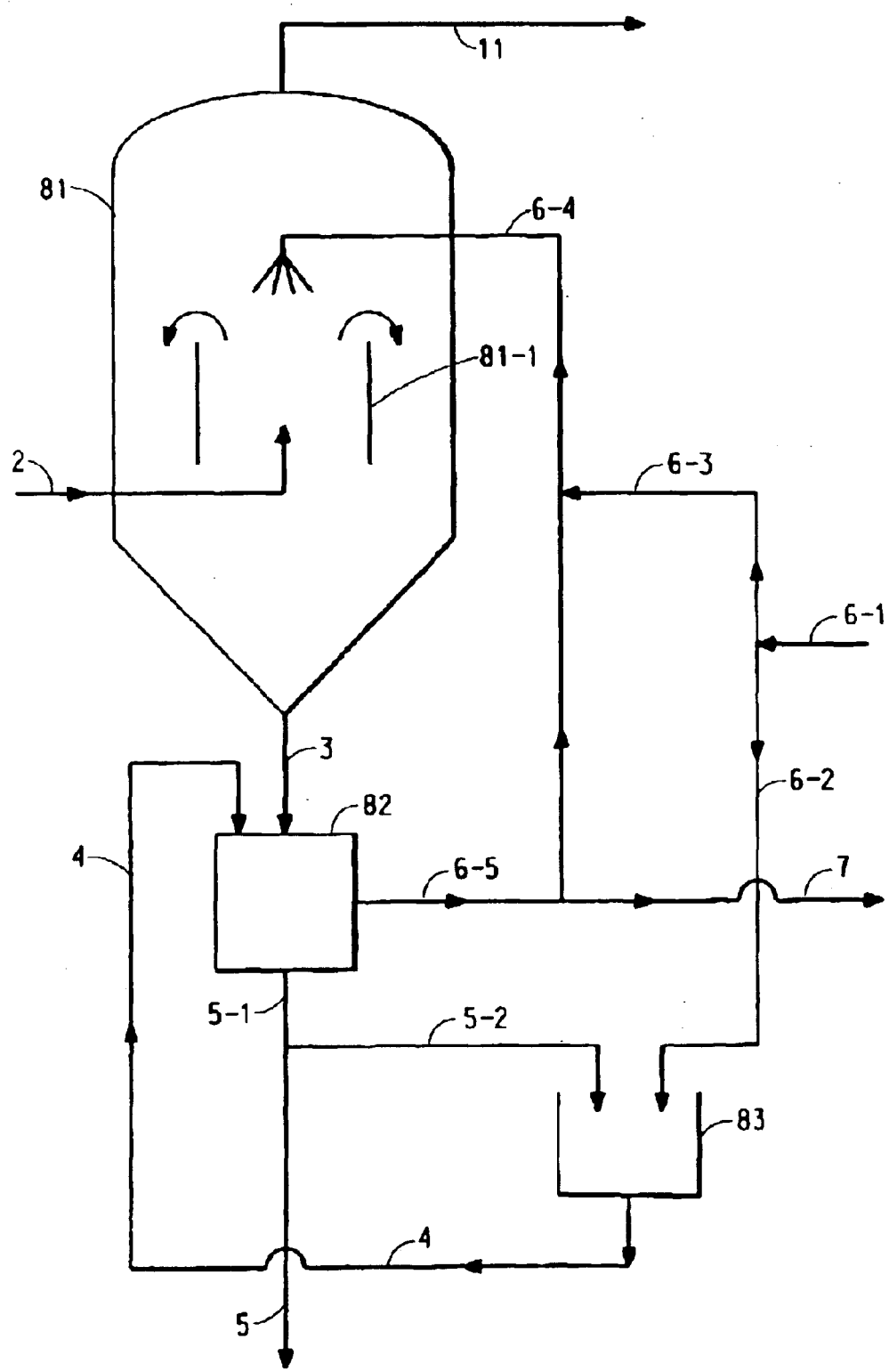
FIG. 2 is a schematic representation of a preferred embodiment of the process of the present invention.

A preferred embodiment of the process of the present invention, and equipment therefor, is described below and illustrated schematically in FIG. 2.

A vapor stream at elevated temperature comprising dianhydro sugar alcohol and water vapor is fed via line (2) to the condensation-crystallization vessel (81) and sparged under the draft tube (81-1). The vapor stream is partly condensed by contacting it with the colder condensate pool in the vessel and a spray, via line (6-4), of dianhydro sugar alcohol diluted with cooling water. The vapor stream is thereby cooled to condense virtually all of the dianhydro sugar alcohol as a supersaturated solution. This solution is allowed to form purified crystals in the vessel, resulting in the formation of a slurry. The uncondensed vapor, mostly water, is continuously withdrawn from the vessel via line (11) to maintain the vessel under a reduced pressure. The slurry is circulated within the vessel, up and around the draft tube with the rising vapor bubbles. The slurry is continuously withdrawn from the vessel via line (3), to maintain a substantially steady level in the vessel, and is conducted to centrifuge (82) to separate the product crystals. The product cake is washed in the centrifuge with a concentrated solution of purified dianhydro sugar alcohol from dissolver (83) via line (4) and is discharged from the centrifuge (82) via line (5-1). A minor portion of the crystals is used to prepare the wash solution in dissolver (83) with purified cooling water via line (6-2). The major portion of the washed crystals is the recovered purified dianhydro sugar alcohol product. It is conducted via line (5) for further treatment to suit the desired application. The mother liquor separated in the centrifuge is conducted via line (6-5) for recycle. A small portion of the mother liquor is purged via line (7) to maintain impurities in the condenser-crystallizer at a low level to obtain product crystals of desired purity. Most of the mother liquor is recycled via line (6). It is diluted with cooling water, line (6-3), and sprayed in the vessel via line (6-4). The total quantity of cooling water that enters the system via line (6-1) is controlled to provide the cooling, by its vaporization, so as to maintain the desired condensation and crystallization temperature in the vessel.

In certain applications, it may be desirable to obtain the dianhydro sugar alcohols in the form of a slurry or a solution in a liquid other than water. For example, when isosorbide is to be incorporated into polyethylene terephthalate, it may be desirable to provide it as a solution in ethylene glycol. Such a solution may be prepared by dissolving the purified isosorbide crystals in ethylene glycol. However, for such cases, it may be preferable to employ an embodiment of the partial condensation and crystallization process, wherein the crystallization is conducted in a fluid other than water, such as glycol when isosorbide is to be incorporated into the polyester.

In this embodiment of the process, the vapor stream comprising dianhydro sugar alcohol and water is contacted with a colder stream of a solvent, that may or may not contain water, to cool the vapors below the melting point of dianhydro sugar alcohol. The solvent is a liquid in which the dianhydro sugar alcohol is only partially soluble below its melting point. At such a temperature and under reduced pressure, most of the dianhydro sugar alcohol is condensed, but only very little water.

The solvent is preferably a high boiling liquid, so only a negligible amount is vaporized and lost with the water vapor. For purification by crystallization to be effective, it is preferred that the solvent also be a polar liquid in which the more polar monoanhydro sugar alcohols and other impurities, such as color-forming bodies, are more soluble than the dianhydro sugar alcohol. Examples of such-high boiling solvents are linear glycols such as ethylene glycol and propylene glycol. These are particularly suitable if the end use involves incorporating the dianhydro sugar alcohol product into polyesters. For example, if it is desired to incorporate isosorbide into polyethylene terephthalate, ethylene glycol would be the preferred solvent.

The total quantity of fresh solvent introduced into the process for this purpose is controlled in relation to the dianhydro sugar alcohol to be less than that quantity which could completely solubilize the dianhydro sugar alcohol. The condensate is then a supersaturated solution from which the dianhydro sugar alcohol precipitates as purified crystals. The quantity of fresh solvent is regulated to obtain a slurry of crystals that can be handled easily. The slurry is withdrawn from the condenser-crystallizer vessel. The purified crystals are separated from the slurry by means such as filtration and centrifugation, and the mother liquor is recycled back to the vessel for contacting with the vapor. To maintain the desired condensation temperature, the heat produced from cooling the vapor, condensing the dianhydro sugar alcohol, and crystallizing the dianhydro sugar alcohol must be removed. This can be accomplished by introducing a chilled stream of fresh solvent (e.g., a refrigerated glycol stream), cooling the slurry with an internal or external recirculation heat exchanger, cooling the recycle mother liquor, or simply introducing cooling water (either separately or along with the fresh solvent or with the recycle mother liquor) and removing the heat through evaporation of this water under the operating conditions of the condenser-crystallizer. The process is preferably conducted continuously so that the condenser vessel's input and output streams are regulated at a substantially constant rate and are coordinated so as to maintain a steady reduced pressure and a steady slurry level in the vessel.

When the dianhydro sugar alcohol is isosorbide and the solvent is ethylene glycol, the operating temperature for the embodiment of the process described above may be from about 20° C. to 57° C. The solubility of isosorbide in ethylene glycol at these temperatures ranges from about 60 to about 93% by weight. A preferred temperature range is 25° C. to 50° C., with the corresponding isosorbide solubility about 65 to about 87% by weight. The operating pressure may be from 5 mm Hg to about 50 mm Hg, preferably 10 to 30 mm Hg. Generally, a higher temperature and lower pressure are preferred so as not to condense much water from the vapor stream. The vapor pressure of ethylene glycol in the above preferred temperature range is less than 1 mm Hg; thus, very little of it is vaporized into the water vapor. The small amount of ethylene glycol contaminating the water stream maybe removed before disposing of the water stream by feeding it to a glycol-water separation column.

The purified isosorbide crystals recovered from the process may be dissolved in a terephthalic acid slurry preparation tank or redissolved in ethylene glycol, either for use as a solution or for further purification treatment.

One skilled in the art will understand that the partial condensation methods disclosed herein could also be advantageously practiced to recover most of the dianhydro sugar alcohol from a vapor stream as a concentrated solution if further purification is not needed for the intended use, or if a concentrated solution is desired for conducting purification by means other than the in situ simultaneous crystallization described here. Recovery by partial condensation would be advantageous in such cases, as it would eliminate the costs associated with condensing all of the vapor stream and then having to vaporize most of the condensed water in a subsequent step.

EXAMPLE

Manufacture of Purified Isosorbide at Nominal 18 Million lb/year

The condensation-crystallization vessel is 9 ft. diameter× 12 ft. high, equipped with spray nozzles and draft tube.

A vapor stream produced by the reaction of sorbitol to isosorbide and separation of the isosorbide from the reaction mass is continuously fed to the condensation-crystallization vessel via line (2) at a rate of 11,100 lb/hr. It contains about 25% by weight isosorbide and feeds isosorbide to the vessel at a rate of 2760 lb/hr. Most of the isosorbide is condensed from the stream by contacting it with the pool of slurry and the diluted recycle mother liquor via line (6-4) spray, as described above. The isosorbide is allowed to crystallize in the vessel. The temperature of the slurry pool is controlled at about 39–42° C. by regulating the flow of fresh, demineralized water into the system via line (6-1) at about 1245 lb/hr. The pressure in the vessel is maintained at 14–15 mm Hg by continuously withdrawing the water vapors from the vessel via line (11). Isosorbide slurry containing about 15% by weight isosorbide crystals is continuously withdrawn via line (3) from the vessel at a rate of 15,330 lb/hr. The slurry is maintained at a steady level in the vessel near the top of the draft tube (81-1). The slurry stream comprises about 2300 lb/hr isosorbide crystals and about 13,030 lb/hr mother liquor. The mother liquor is about 95% by weight isosorbide.

The crystals are separated and washed with wash liquor in centrifuge (82) and discharged as a 70% solids cake via line (5-1). The mother liquor is recycled via line (6-5). Some of the mother liquor is purged via line (7) at a rate of about 480 lb/hr and recycled back to the reaction-separation step. The rest, via line (6), is diluted with the cooling water of line (6-3) and is sprayed inside the vessel via line (6-4) to contact the vapors. The centrifuged cake contains isosorbide crystals of greater than 99.8% purity which are substantially free from color forming impurities. A portion of the cake is used for making the wash liquor, and the remainder is transported via line (5) for further processing at a rate of about 2527 lb/hr. On a dry basis, it contains about 2300 lbs/hr of purified isosorbide for the nominal 18 million lbs/year production.

What is claimed is:

1. A process for the recovery and purification of dianhydro sugar alcohol from a vapor stream comprising the dianhydro sugar alcohol and water, comprising:
    a) introducing a vapor stream comprising dianhydro sugar alcohol and water into a condensation-crystallization vessel maintained at a pressure of 5-30 mm Hg and at a temperature below the melting point of the dianhydro sugar alcohol;
    b) partially condensing the vapor stream to precipitate the dianhydro sugar alcohol as a slurry of high purity dianhydro sugar alcohol crystals in a supersaturated mother liquor;
    c) removing uncondensed vapors from the condensation-crystallization vessel;
    d) withdrawing the slurry of high purity dianhydrosugar alcohol crystals from the condensation-crystallization vessel; and
    e) separating the dianhydro sugar alcohol crystals from the mother liquor.

2. The process of claim 1, wherein the steps of introducing the vapor stream, removing the uncondensed water vapors, and withdrawing the slurry are conducted continuously, and the dianhydro sugar alcohol is recovered and purified continuously.

3. The process of claim 2, wherein the rates of introducing the vapor stream, removing the uncondensed vapors and withdrawing the slurry are coordinated to maintain a steady level in the vessel.

4. The process of claim 1, wherein the dianhydro sugar alcohol is isosorbide.

5. The process of claim 4, wherein the condensation is conducted at a temperature from 20° C. to 50° C.

6. The process of claim 1, wherein the mother liquor is recycled to the condensation-crystallization vessel.

7. The process of claim 1, further comprising crystallization of dianhydrosugar alcohol from the mother liquor.

8. A process for the recovery and purification of dianhydro sugar alcohols from a continuous vapor stream comprising a dianhydro sugar alcohol and water, comprising partially condensing the vapor stream at a temperature below the melting point of the dianhydro sugar alcohol and a pressure of 5 to 30 mm Hg, wherein the dianhydro sugar alcohol is condensed as a supersaturated solution and forms high purity crystals.

9. The process of claim 8, wherein the partial condensation is conducted continuously.

10. The process of claim 8, wherein the dianhydro sugar alcohol is isosorbide.

11. The process of claim 1, wherein the condensation is conducted at a temperature from 20 to 50° C. 20° C. to 50° C.

12. A process for the recovery and purification of dianhydro sugar alcohols from a vapor stream comprising a dianhydro sugar alcohol and water, comprising contacting the vapor stream with a liquid stream comprising one or more high boiling, polar solvents in which the dianhydro sugar alcohol is only partly soluble, and condensing, at a pressure of 5–50 mm Hg and a temperature lower than the melting point of the dianhydro sugar alcohol, the dianhydro sugar alcohol.

13. The process of claim 12, wherein the amount of high boiling, polar solvent added is less than the quantity required to produce a supersaturated solution of dianhydro sugar alcohol.

14. The process of claim 12, wherein the high boiling, polar solvent has a boiling point in the range 170° C. to 270°C.

15. The process of claim 12, wherein the condensation is conducted at a pressure in the range 5 to 50 mm Hg and at a temperature in the range of 25° C. to 50° C.

16. The process of claim 12, wherein the dianhydro sugar alcohol is isosorbide.

17. The process of claim 12, wherein the high boiling, polar solvent comprises one or more linear diols.

18. The process of claim 13, wherein the supersaturated solution is allowed to form crystals, the crystals are separated from the solution and the mother liquor is recycled.

19. A continuous process for the recovery and purification of dianhydro sugar alcohol from a vapor stream comprising the dianhydro sugar alcohol and water, comprising:

a) continuously feeding the vapor stream of water and dianhydro sugar alcohol to a condensation vessel maintained at a temperature below the melting point of the dianhydro sugar alcohol and a pressure of 5 to 50 mm Hg;

b) continuously condensing the vapor stream to condense the dianhydro sugar alcohol as a supersaturated solution;

c) allowing a portion of the dianhydro sugar alcohol to precipitate as dianhydro sugar alcohol crystals, to produce a slurry of dianhydro sugar alcohol crystals in a supersaturated solution;

d) continuously withdrawing the slurry of dianhydro sugar alcohol crystals from the vessel;

e) continuously withdrawing the uncondensed vapors from the condensation vessel to maintain a pressure of 5–50 mm Hg;

f) continuously condensing the uncondensed vapors in a secondary condenser connected to a vacuum source to withdraw any noncondensibles;

g) continuously separating the dianhydro sugar alcohol crystals from the slurry and h) recycling the mother liquor back to the condensation vessel.

* * * * *